US010016397B2

(12) United States Patent
Springer et al.

(10) Patent No.: US 10,016,397 B2
(45) Date of Patent: Jul. 10, 2018

(54) SELECTIVE AT2 RECEPTOR AGONISTS FOR USE IN TREATMENT OF CACHEXIA

(71) Applicant: Charité-Universitaetsmedizin Berlin, Berlin (DE)

(72) Inventors: Jochen Springer, Falkensee (DE); Stefan Anker, Berlin (DE); Andrew JS Coats, St. Kilda (AU)

(73) Assignee: CHARITÉ—UNIVERSITAETSMEDIZN BERLIN, Berlin (DE)

( * ) Notice: Subject to any disclaimer, the term of this patent is extended or adjusted under 35 U.S.C. 154(b) by 0 days.

(21) Appl. No.: 14/908,165

(22) PCT Filed: Jul. 17, 2014

(86) PCT No.: PCT/EP2014/065417
§ 371 (c)(1),
(2) Date: Jan. 28, 2016

(87) PCT Pub. No.: WO2015/014634
PCT Pub. Date: Feb. 5, 2015

(65) Prior Publication Data
US 2016/0175286 A1    Jun. 23, 2016

(30) Foreign Application Priority Data

Jul. 29, 2013   (EP) .................................... 13178319

(51) Int. Cl.
| A61K 45/06 | (2006.01) |
| A61K 31/4178 | (2006.01) |
| A61K 31/417 | (2006.01) |
| C07D 409/10 | (2006.01) |

(52) U.S. Cl.
CPC ........ *A61K 31/4178* (2013.01); *A61K 31/417* (2013.01); *A61K 45/06* (2013.01); *C07D 409/10* (2013.01)

(58) Field of Classification Search
CPC .............................. C07D 231/12; A61K 45/06
See application file for complete search history.

(56) References Cited

U.S. PATENT DOCUMENTS

| 7,652,054 | B2 * | 1/2010 | Alterman | ............. | C07D 231/12 |
| | | | | | 514/396 |
| 8,835,471 | B2 * | 9/2014 | Steckelings | ........ | A61K 31/4178 |
| | | | | | 514/365 |
| 2009/0117197 | A1 | 5/2009 | Sznaidman et al. | | |
| 2012/0035232 | A1 | 2/2012 | Steckelings et al. | | |

FOREIGN PATENT DOCUMENTS

| WO | 9920260 | | 4/1999 |
| WO | 9920260 | A2 | 4/1999 |
| WO | 0021509 | A2 | 4/2000 |
| WO | 02096883 | | 12/2002 |
| WO | 02096883 | A1 | 12/2002 |
| WO | 2006109048 | | 10/2006 |
| WO | 2006109048 | A1 | 10/2006 |
| WO | 2007083119 | | 7/2007 |
| WO | 2007083119 | A2 | 7/2007 |

OTHER PUBLICATIONS

Murugaiah et al., Journal of Medicinal Chemistry (2012), 55(5), 2265-2278.*
Mahalingam et al., Bioorganic & Medicinal Chemistry (2010), 18(12), 4570-4590.*
International Search Report from PCT/EP2014/065417 dated Sep. 30, 2014.
Song, Yao-hua et al.: "Muscle-specific expression of IGF-1 blocks angiotensin Il-induced skeletal muscle wasting", Journal of Clinical Investigation, vol. 115, No. 2, Jan. 13, 2005, pp. 451-458.
Springer, J. et al.: "The Xanthane Oxidase Inhibitors Oxypurinol and Allopurinol Reduce Wasting and Improve Cardiac Function in Experimental Cancer Cachexia", Journal of Carial Failure, vol. 15, No. 6, Aug. 1, 2009, p. S22.
Kuroda, K. et al.: "Prevention of Cancer Cachexia by a Novel Nuclear Factor B Inhibitor in Prostate Cancer", Clinical Cancer Research, vol. 11, No. 15, Aug. 1, 2005, pp. 5590-5594.
Maamary, Jad R. et al.: 574. Models of Cancer Cachexia: Treatment with Inhibition of NF-kB 11, Molecular Therapy, vol. 13, May 1, 2006, pp. S221-S221.
Olivan, Mireia et al.: "Theophylline is able to partially revert cachexia in tumour-bearing rats", Nutrition & Metabolism, Biomed Central, vol. 9, No. 1, Aug. 21 2012, p. 76.
Kung, Thomas et al.: "Novel treatment approaches to cachexia and sarcopenia: highlights from the 5th Cachexia conference", Expert Opinion on Investigational Drugs, vol. 19, No. 4, Apr. 1, 2010, pp. 579-585.
Argiles, Josep M. et al.: "Optimal management of cancer anorexia-cachexia syndrome", Cancer Management and Research, vol. 2, No. 1, Jan. 22, 2010, pp. 27-38.
Rompe, F. et al.: "Direct Angiotensin II Type 2 Receptor Stimulation Acts Anti-Inflammatory Through Epoxyeicosatrienoic Acid and Inhibition of Nuclear Factor B", Hypertension, vol. 55, No. 4, Apr. 1, 2010, pp. 924-931.
Steckelings, Muscha et al: "Non-peptide AT2-receptor agonists", Current Opinion in Pharmacology, vol. 11, No. 2, Apr. 1, 2011, pp. 187-192.
Kaschina, E. et al.: "Angiotensin II Type 2 Receptor Stimulation: A Novel Option of Therapeutic Interference With the Renin-Angiotensin System in MyocardialInfarction?", Circulation, vol. 118, No. 24, Dec. 9, 2008, pp. 2523-2532.
Ohshima, Kousei et al.: "Direct Angiotensin II Type 2 Receptor Stimulation Ameliorates Insulin Resistance in Type 2 Diabetes Mice with PPAR[gamma] Activation", Plos One, vol . 7, No. 11, Nov. 14, 2012, p. e48387.
Matavelli, L.C. et al: "Angiotensin AT2 Receptor Stimulation Inhibits Early Renal Inflammation in Renovascular Hypertension", Hypertension, vol. 57, No. 2, Feb. 1, 2011, pp. 308-313.
Wu et al.: "Selective Angiotensin II AT2 Receptor Agonists: Arylbenzylimidazole Structure-Activity Relationships", Journal of Medicinal Chemistry, American Chemical Society, vol. 49, No. 24, Nov. 9, 2006, pp. 7160-7168.
Yao-Hua Song et al: "Muscle-specific expression of IGF-1 blocks angiotensin II-induced skeletal muscle wasting", Journal of Clinical Investigation, vol. 115, No. 2, Jan. 13, 2005 (Jan. 13, 2005), pp. 451-458.
Springer J et al: "The Xanthine Oxidase Inhibitors Oxypurinol and Allopurinol Reduce Wasting and Improve Cardiac Function in Experimental Cancer Cachexia", Journal of Cardial Failure, Churchill Livingstone, Naperville, IL, US, vol. 15, No. 6, Aug. 1, 2009 (Aug. 1, 2009), p. S22.
K. Kuroda et al: "Prevention of Cancer Cachexia by a Novel Nuclear Factor B Inhibitor in Prostate Cancer", Clinical Cancer Research, vol. 11, No. 15, Aug. 1, 2005.

(Continued)

*Primary Examiner* — Paul V Ward
(74) *Attorney, Agent, or Firm* — Fox Rothschild LLP

(57) ABSTRACT

The present invention is directed to selective AT2 receptor agonist or a pharmaceutically acceptable salt thereof for use in treatment of cachexia, preferably for use in treatment of cancer cachexia.

20 Claims, 18 Drawing Sheets

(56) References Cited

OTHER PUBLICATIONS

Figure 1:
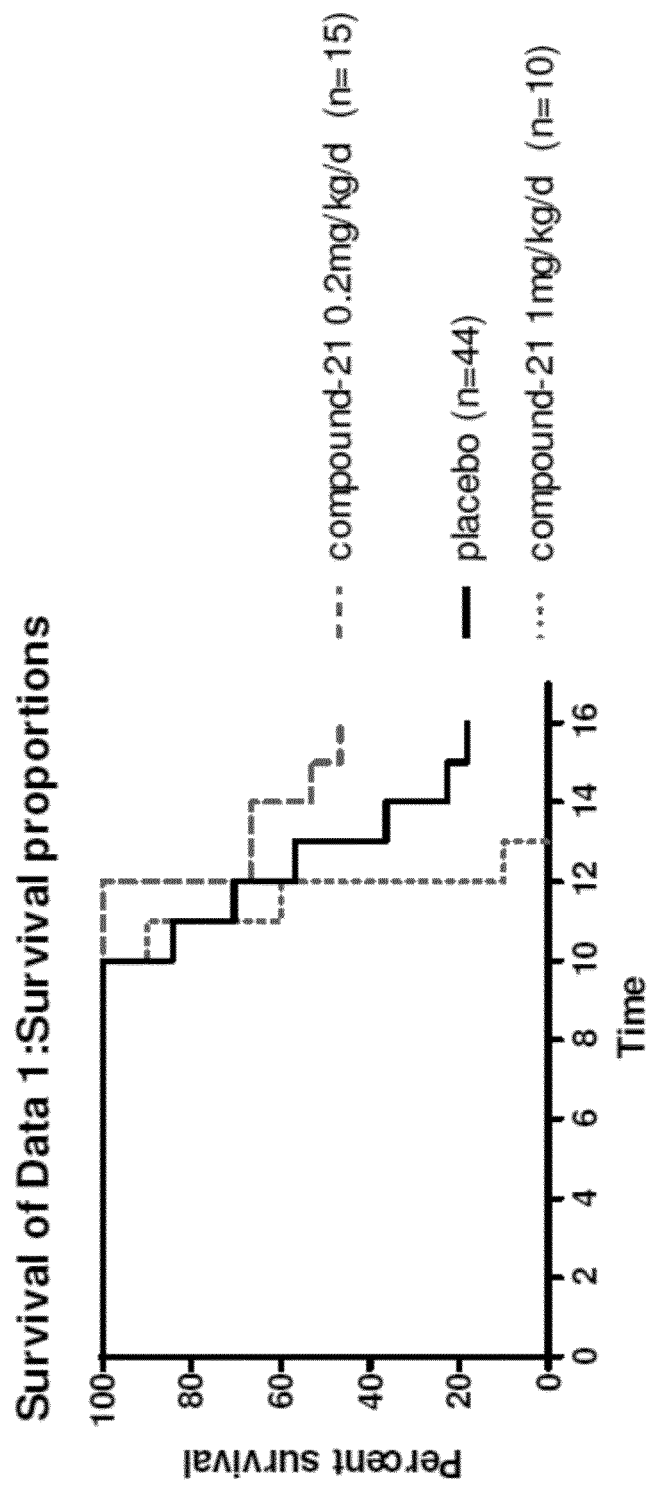

Jad R. Maamary et al: "574. Models of Cancer Cachexia: Treatment with Inhibition of NF-kB", Molecular Therapy, vol. 13, May 1, 2006 (May 1, 2006), pp. S221-S221.

Mireia Olivan et al: "Theophylline is able to partially revert cachexia in tumour-bearing rats", Nutrition & Metabolism, Biomed Central. London, GB, vol. 9, No. 1, Aug. 21, 2012 (Aug. 21, 2012), p. 76.

Kung Thomas et al: "Novel treatment approaches to cachexia and sarcopenia: highlights from the 5th Cachexia Conference", Expert Opinion on Investigational Rugs, Ashley Publications Ltd., London, GB, vol. 19, No. 4, Apr. 1, 2010 (Apr. 1, 2010), pp. 579-585.

Josep M Argiles et al: "Optimal management of cancer anorexi-acachexia syndrome", Cancer Management and Research, vol. 2, No. 1, Jan. 22, 2010.

F. Rompe et al: "Direct Angiotensin II Type 2 Receptor Stimulation Acts Anti-Inflammatory Through Epoxyeicosatrienoic Acid and Inhibition of Nuclear Factor B", Hypertension, vol. 55, No. 4, Apr. 1, 2010 (Apr. 1, 2010), pp. 924-931.

Muscha Steckelings et al: "Non-peptide AT2-receptor agonists", Current Opinion in Pharmacology, vol. 11, No. 2, Apr. 1, 2011 (Apr. 1, 2011).

E. Kaschina et al: "Angiotensin II Type 2 Receptor Stimulation: A Novel Option of Therapeutic Interference With the Renin-Angiotensin System in Myocardial Infarction?", Circulation, vol. 118, No. 24, Dec. 9, 2008 (Dec. 9, 2008), pp. 2523-2532.

Kousei Ohshima et al: "Direct Angiotensin II Type 2 Receptor Stimulation Ameliorates Insulin Resistance in Type 2 Diabetes Mice with PPAR[gamma] Activation", PLOS ONE, vol. 7, No. 11, Nov. 14, 2012 (Nov. 14, 2012), p. e48387.

L. C. Matavelli et al: "Angiotensin AT2 Receptor Stimulation Inhibits Early Renal Inflammation in Renovascular Hypertension", Hypertension, vol. 57, No. 2, Feb. 1, 2011 (Feb. 1, 2011), pp. 308-313.

Xiongyu Wu et al: "Selective Angiotensin II AT2 Receptor Agonists: Arylbenzylimidazole Structure-Activity Relationships", Journal of Medicinal Chemistry, American Chemical Society, vol. 49, No. 24, Nov. 9, 2006 (Nov. 9, 2006), pp. 7160-7168.

* cited by examiner

SELECTIVE AT2 RECEPTOR AGONISTS FOR USE IN TREATMENT OF CACHEXIA

CROSS-REFERENCE TO RELATED APPLICATIONS

This application is a § 371 U.S. National Stage of International Application No. PCT/EP2014/065417, filed Jul. 17, 2014, which claims priority to and the benefit of European Application No.: 13178319.3, filed Jul. 29, 2013, the entireties of which are both hereby incorporated herein by reference.

Cachexia is a severe complication of multiple separate illnesses and an area of significant unmet medical need. Successful treatment or prevention of cachexia may lead to improved quality of life and prolonged life expectancy in affected patients.

It has already been described that the renin-angiotensin system (RAS) is involved in development of cachexia, see e.g. WO 99/20260.

The octapeptide angiotensin II is the main biologically active component of the renin-angiotensin-system (RAS) in humans. Angiotensin II mediates its actions via two main receptors—the AT1 and AT2 receptors. Angiotensin II binds with equal affinity to both receptors, but because of the predominant expression of the AT1 receptor, angiotensin II predominantly elicits AT1 mediated responses. The AT1 receptor is closely associated with the regulation of blood pressure, fluid and electrolyte balance, as well as thirst. The AT2 receptor has a lower expression in adult tissues than the AT1 receptor and may be up-regulated in pathological conditions such as heart failure, renal failure, myocardial infarction, brain lesions, vascular injury and wound healing. Recently, it has been described that the AT2 receptor acts in anti-proliferative, anti-inflammatory, anti-fibrotic and anti-apoptotic ways. These features are in contrast to what is usually associated with RAS activation, such as hypertension, inflammation, fibrosis and end-organ damage, all of which are mediated by the AT1 receptor. The tissue protective properties of AT2 receptor activation have been reported in stroke, myocardial infarction and artherosclerosis. An inhibition of NFkB signaling after AT2 receptor stimulation involving the production of epoxyeicosatrienoic acid (which resulted in a reduction of the pro-inflammatory IL-6) has been reported.

It has been reported that cachexia is associated with elevated angiotensin II levels and/or increased activity of the RAS. Current approaches targeting angiotensin II and RAS have concentrated on the inhibition of angiotensin-converting enzyme (ACE) and on the use of AT1 receptor antagonists, see WO 99/20260, US 2009/0117197 A1 and WO 00/21509. Indeed, the use of the ACE inhibitors enalapril and imidapril has already been shown to be effective in treatment of cachexia related to chronic heart failure.

However, current strategies for the treatment of cachexia are still sub-optimal, limited in effectiveness and associated with potentially treatment-limiting side effects. Thus, there is a need for further options for the effective treatment of cachexia.

According to the invention, selective AT2 receptor agonists or pharmaceutically acceptable salts thereof are provided for use in the treatment of cachexia.

Despite current knowledge teaching the use of ACE inhibitors and AT1 receptor antagonists, it has surprisingly been found that administration of selective AT2 receptor agonists is effective in treating cachexia. Selective AT2 receptor agonists have been found to improve one or more features of cachexia, including a reduction in muscle wasting, a preservation of fat mass and improvements of quality of life.

Cachexia, also called the wasting syndrome, is a severe condition which is frequently associated with a poor prognosis. Cachexia can be characterized by loss of weight, muscle atrophy, fatigue, weakness and/or significant loss of appetite in someone who is not actively trying to lose weight. In formal terms, cachexia is defined by MeSH (2009) ID D002100 and exhibits the symptoms of loss of body mass that cannot be reversed nutritionally. Even if the affected patient eats more calories, body mass will be lost. In most cases cachexia is secondary to another primary pathology in the patient. Cachexia can be associated with cancer, AIDS, liver cirrhosis, liver failure, chronic renal failure, chronic infection, diabetes, heart disease e.g. such as chronic or congestive heart failure, chronic obstructive lung disease, multiple sclerosis, tuberculosis, familial amyloid polyneuropathy, heavy metal poisoning e.g. such as mercury poisoning, arthritis, motor neuron diseases, burns and hormonal deficiency syndromes. Of particular interest is cachexia associated with cancer, sometimes known as cancer cachexia. Preferably the term cachexia as used herein excludes cachexia associated with inflammatory bowel syndrome/disease.

The present invention is directed to the use of selective AT2 agonists for treating cachexia. As used herein, the term "treating" refers to reversing, alleviating or inhibiting the progression of a disease, disorder or condition, or improvement in one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein "treating" may also refer to preventing the recurrence of a disease, disorder or condition or of one or more symptoms associated with such disease, disorder or condition. The terms "treatment" and "therapeutically," as used herein, refer to the act of treating, as "treating" is defined above.

The present invention is directed to the use of selective AT2 receptor agonists in the treatment of cachexia. Selective AT2 receptor agonists bind selectively to, and exhibit agonist activity at, the AT2 receptor. An AT2 receptor agonist is referred to as being selective to the AT2 receptor if the affinity ratio for that relevant AT2 agonist (AT2:AT1) is at least 5:1, preferably at least 10:1 and more preferably at least 20:1. The skilled person is well aware of compounds that represent selective AT2 receptor agonists in the sense of the present invention and how to produce them; such compounds are well known in the art.

The selective AT2 receptor agonist of the invention may be one of the selective AT2 receptor agonist compounds provided in EP 1 395 566 B1, the disclosure of which is incorporated herein by reference.

According to the invention, the selective AT2 receptor agonist is preferably a compound of formula I or a pharmaceutically acceptable salt thereof, with formula I:

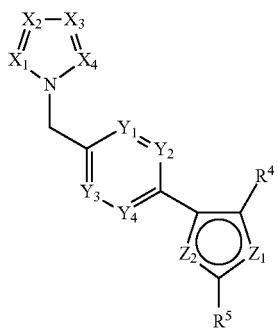

wherein
one of $X_1$ and $X_2$ represents —N— and the other represents —C($R^1$)—;
$X_3$ represents —N— or —C($R^2$)—;
$X_4$ represents —N— or —C($R^3$)—;
$R^1$, $R^2$ and $R^3$ independently represent H, $C_{1-6}$ alkyl, $C_{1-6}$ alkoxy, $C_{1-6}$ alkoxy-$C_{1-6}$-alkyl or halo; provided that, when $X_1$ represents —C($R^1$)—, $X_3$ represents —C($R^2$)— and $X_4$ represents —C($R^3$)—, then $R^1$ represents H;
$Y_1$, $Y_2$, $Y_3$ and $Y_4$ independently represent —CH— or —CF;
$Z_1$ represents —CH—, —O—, —S—, —N— or —CH=CH—;
$Z_2$ represents —CH—, —O—, —S— or —N—;
provided that:
(a) $Z_1$ and $Z_2$ are not the same;
(b) when $Z_1$ represents —CH=CH—, then $Z_2$ may only represent —CH— or N—; and
(c) other than in the specific case in which $Z_1$ represents —CH=CH—, and $Z_2$ represents —CH—, when one $Z_1$ and $Z_2$ represents —CH—, then the other represents —O— or —S—;
$R^4$ represents —S(O)$_2$N(H)C(O)$R^6$, —S(O)$_2$N(H)S(O)$_2$$R^6$, —C(O)N(H)S(O)$_2$$R^6$, or, when $Z_1$ represents —CH=CH—, $R^4$ may represent —(H)S(O)$_2$N(H)C(O)$R^7$ or —N(H)C(O)N(H)S(O)$_2$$R^7$;
$R^5$ represents $C_{1-6}$ alkyl, $C_{1-6}$ alkoxy, $C_{1-6}$ alkoxy-$C_{1-6}$-alkyl or di-$C_{1-3}$alkylamino-$C_{1-4}$-alkyl;
$R^6$ represents $C_{1-6}$ alkyl, $C_{1-6}$ alkoxy, $C_{1-6}$ alkoxy-$C_{1-6}$-alkyl, $C_{1-3}$ alkoxy-$C_{1-6}$-alkoxy, $C_{1-6}$ alkylamino or di-$C_{1-6}$ alkylamino; and
$R^7$ represents $C_{1-6}$ alkyl,
wherein
alkyl groups, and the alkyl parts of alkoxy, alkoxyalkyl, alkoxyalkoxy, alkylamino and alkylaminoalkyl groups, as defined herein may be straight-chain or, when there is a sufficient number (i.e. a minimum of three) of carbon atoms, be branched-chain, and/or cyclic; or when there is a sufficient number (i.e. a minimum of four) of carbon atoms, such groups may also be part cyclic/acyclic; or alkyl groups, and alkyl parts of alkoxy, alkoxyalkyl, alkoxyalkoxy, alkylamino and alkylaminoalkyl groups, may also be saturated or, when there is a sufficient number (i.e. a minimum of two) of carbon atoms, be unsaturated; or such groups may also be substituted by one or more halo, and especially fluoro, atoms.

Pharmaceutically-acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo or by freeze-drying). Salts may also be prepared by exchanging a counter-ion of a compound of the invention in the form of a salt with another counter-ion, for example using a suitable ion exchange resin.

For the avoidance of doubt, alkoxy and alkoxyalkoxy groups are attached to the rest of the molecule via the oxygen atom in that group, alkylamino groups are attached to the rest of the molecule via the nitrogen atom of the amino part of that group and alkylaminoalkyl and alkoxyalkyl groups are attached to the rest of the molecule via the alkyl part of that group.

The term "halo", when used herein, includes fluoro, chloro, bromo and iodo.

Preferred ring systems comprising the substituents $Y_1$, $Y_2$, $Y_3$ and $Y_4$ include phenyl groups. For the avoidance of doubt, the ring systems in compounds of formula I that comprise the groups $Z_1$ and $Z_2$, are aromatic in nature. In some instances, for example in cases where one or more of $Z_1$ and $Z_2$ represent —CH— or —N—, the skilled person will appreciate that an additional H atom may necessarily be bonded to that CH group or N atom, in order to ensure that the rules of valency are adhered to. Preferred ring systems comprising $Z_1$ and $Z_2$ include oxazole groups, thiazole groups, phenyl groups, pyridinyl groups, thiophenyl groups and furanyl groups.

In this respect, compounds of formula I may exhibit tautomerism. All tautomeric forms and mixtures thereof are included within the scope of the invention.

Compounds of formula I also contain one or more asymmetric carbon atoms and may therefore exhibit optical and/or diastereoisomerism.

Diastereoisomers may be separated using conventional techniques, e. g. chromatography or fractional crystallisation. The various stereoisomers may be isolated by separation of a racemic or other mixture of the compounds using conventional, e. g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e. g. HPLC, chromatography over silica). All stereoisomers are included within the scope of the invention.

Preferred compounds of formula I include those in which:
(i) when $X_1$ represents —C($R^1$)—, then:
    (a) $X_3$ represents —C($R^2$)— and $X_4$ represents —N—;
    (b) $X_3$ and $X_4$ both represent N; or
    (c) $X_3$ represents —C($R^2$)— and $X_4$ represents —C($R^3$)—; or
(ii) when $X_1$ represents —N—, then:
    (a) $X_3$ represents —N—; or
    (b) $X_3$ represents —C($R^2$) and $X_4$ represents —C($R^3$)—.

In case (i) (a) above, it is further preferred that $R^1$ represents H.

In case (ii) (a) above, when $X_4$ represents —C($R^3$)—, it is further preferred that $R^3$ represents H.

Preferred compounds of formula I include those in which:

$R^1$ represents $C_{1-3}$ alkyl, such as ethyl, —$CF_3$ or, especially, H;

$R^2$ represents $C_{1-3}$ alkyl, such as methyl, halo, or, especially, H;

$R^3$ represents $C_{1-3}$ alkyl, halo or, especially, H;

$Y_1$, $Y_2$, $Y_3$ and $Y_4$ all represent —CH—;

Z1 represents —S— or —CH=CH—;

Z2 represents —CH—;

$R^4$ represents $S(O)_2N(H)C(O)R^6$;

$R^5$ represents n-butyl or, particularly, iso-butyl;

$R^6$ represents n-butoxymethyl, iso-butoxy and especially, n-butoxy.

Preferred ring systems comprising the substituents $X_1$, $X_2$, $X_3$ and $X_4$ include pyrazole groups, imidazole groups, 1,2,4-triazole groups and tetrazol groups.

Compounds of formula I that may be mentioned include those in which, when $X_1$, $X_3$ and $X_4$ all represent —CH—, $Y_1$, $Y_2$, $Y_3$ and $Y_4$ all represent —CH—, Z1 represents —CH=CH— or, particularly, —S—, $Z_2$ represents —CH— and represents n-butyl or, particularly, iso-butyl, then $R^4$ represents —$S(O)_2N(H)C(O)R^6$, in which $R^6$ represents —O-iso-propyl (i.e. iso-propoxy), —O-iso-butyl (i.e. iso-butoxy), —$CH_2$—O-n-butyl (i.e. n-butoxymethyl) or, particularly, —O-n-butyl (i.e. n-butoxy).

Compounds of formula I that may further be mentioned include those in which, when $X_1$, $X_3$ and $X_4$ all represent —CH—, $Y_1$, $Y_2$, $Y_3$ and $Y_4$ all represent —CH—, $Z_1$ represents —CH=CH— or —S—, $Z_2$ represents —CH— and $R^5$ represents n-butyl or iso-butyl, then $R^4$ does not represent —$S(O)_2N(H)C(O)R^6$, in which $R^6$ represents —O-iso-propyl, —O-iso-butyl, —$CH_2$—O-n-butyl or —O-n-butyl.

Further compounds of formula I that may be mentioned include those in which:

$R^4$ does not represent —$S(O)_2N(H)S(O)2R^6$;

$R^5$ does not represent di-$C_{1-3}$ alkylamino-$C_{1-4}$-alkyl;

$R^6$ does not represent $C_{1-3}$ alkoxy-$C_{1-6}$ alkoxy.

In a particular preferred embodiment the compound of formula I is the compound,
wherein
$X_2$ is —N—;
$X_1$, $X_3$ and $X_4$ are —CH—;
$Y_1$, $Y_2$, $Y_3$, $Y_4$ are —CH—;
$Z_1$ is —S—;
$Z_2$ is —CH—;
$R^4$ is —$S(O)_2N(H)C(O)R^6$;
$R^5$ is iso-butyl; and
$R^6$ is-O-n-butyl.

This preferred compound (also referred to as compound 21) has the structure:

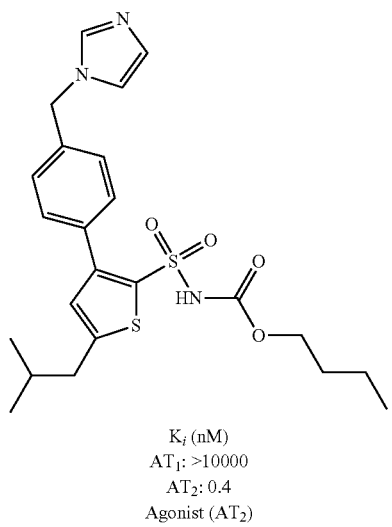 [SMILES: CCCCOC(=O)NS(=O)(=O)c1sc(CC(C)C)cc1-c1ccc(Cn2ccnc2)cc1]

$K_i$ (nM)
$AT_1$: >10000
$AT_2$: 0.4
Agonist ($AT_2$)

Above mentioned preferred compound 21 is a selective AT2 receptor agonist and exhibits $K_i$ of 0.4 nM for AT2 receptor whereas the $K_i$ for AT1 receptor is >10,000 nM.

Compounds of formula I may be made in accordance with techniques well known to those skilled in the art, for example as described in EP 1 395 566 B1.

According to the present invention, the selective AT2 receptor agonist is administered preferably at an effective dose. An "effective dose" is the dose of a selective AT2 receptor agonist that upon administration to a patient yields a measurable therapeutic effect with regard to the disease of interest. In the present invention an effective dose is the dose of a selective AT2 receptor agonist that upon administration to a patient yields a therapeutic effect with regard to at least one cachexia related symptom in a patient or patients suffering from cachexia. Preferably, the selective AT2 receptor agonist is administered at a dose of not more than 10 mg/kg body weight per treatment or administration. In particular, the selective AT2 receptor agonist can be administered at a dose of 0.1 μg/kg to 5000 μg/kg body weight per treatment or administration, preferably of 1 μg/kg to 2000 μg/kg body weight per treatment or administration. In order to prevent acute side effects to occur, it is recommended that the selective AT2 receptor agonist is administered at a maximum cumulative daily dose of not more than 10 mg/kg body weight.

In any event, the physician or the skilled person will be able to determine the actual dose which will be suitable for an individual patient, which is likely to vary with the age, weight, sex, and concomitant illnesses such as renal or hepatic dysfunction and response of the particular patient to be treated. The above mentioned dosages are exemplary of the average case. There can, of course, be individual instances where higher or lower dosage ranges are appropriate, and such are within the scope of the invention.

The selective AT2 receptor agonist will normally be administered orally, intravenously, subcutaneously, bucally, rectally, dermally, nasally, tracheally, bronchially or by any other parenteral route or via inhalation in a pharmaceutically acceptable dosage form.

The present invention is also directed to a method of treatment of cachexia, wherein a patient in need of such therapy is administered an effective dose of a selective AT2 receptor agonist or a pharmaceutically acceptable salt thereof.

The present invention is also directed to the use of a selective AT2 receptor agonist in the manufacture of a medicament for treatment of cachexia.

When used in human therapy, the selective AT2 receptor agonist of the invention and their pharmaceutically acceptable salts will generally be administered as a formulation in association with one or more pharmaceutically acceptable excipients. The term "excipient" is used herein to describe any ingredient other than the compound of the invention, The choice of excipient will to a large extent depend on the particular mode of administration.

The selective AT2 receptor agonist of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include: solid formulations such as tablets; capsules containing particulates, liquids, or powders; lozenges (including liquid-filled); and chews; multi- and nano-particulates; gels; solid solutions; liposomes; films, ovules, sprays and liquid formulations. Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

The selective AT2 receptor agonist of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art.

The selective AT2 receptor agonist of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol.

The selective AT2 receptor agonist of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin. The pressurised container, pump, spray, atomizer, or nebuliser contains a solution or suspension of the selective AT2 receptor agonist of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

The use of selective AT2 receptor agonists in the treatment of cachexia may have the advantage that such compounds may be more efficacious than, be less toxic than, be longer acting than, be more potent than, produce fewer side effects than, be more easily absorbable than, have better pharmacokinetic profile (e.g. higher oral bioavailability and/or lower clearance) than, and/or have other useful pharmacological, physical, or chemical properties over compounds known in the prior art for treatment of cachexia.

In another aspect, the present invention is directed to the use of a selective AT2 receptor agonist for treatment of cachexia in combination with at least one further active pharmaceutical agent. Such combination provide for the administration of selective AT2 receptor agonist and at least one further active pharmaceutical agent, and, thus, may be presented either as separate formulations, wherein at least one formulation comprises the selective AT2 receptor agonist, and at least one other formulation comprises said at least one further active pharmaceutical agent. Alternatively the selective AT2 receptor agonist and the at least one further active pharmaceutical agent may be presented (i.e. formulated) as a combined preparation (i.e. presented as a single formulation comprising both compounds).

Preferably, the at least one further active pharmaceutical agent for combination with selective AT2 receptor agonist is a compound which is suitable for treatment of cachexia or the disease associated with said cachexia.

Preferably, the selective AT2 receptor agonist for use in treatment of cachexia is administered in combination with at least one angiotensin converting enzyme (ACE) inhibitor. The skilled person is well aware of suitable ACE inhibitors. It is particularly referred to ACE inhibitors as disclosed in WO 99/20260. Preferably, the ACE inhibitor is one of captopril, zofenopril, enalapril, ramipril, quinapril, perindopril, lisinopril, benazepril, imidapril, trandolapril, fosinopril, moexipril, cilazapril, spirapril, temocapril, alacepril, ceronapril, delepril, moveltipril, and/or combinations thereof. A particularly preferred ACE inhibitor is imidapril.

Alternatively or in addition, the at least one further active pharmaceutical agent is a selective AT1 receptor antagonist. The skilled person is well aware of suitable AT1 receptor antagonist. It is particularly referred to AT1 receptor antagonist as disclosed in WO 99/20260. Preferably, the AT1 receptor antagonist is one of azilsartan, candesartan, eprosartan, fimasartan, irbesartan, losartan, milfasartan, olmesartan, pomisartan, pratosartan, ripiasartan, saprisartan, tasosartan, telmisartan, valsartan and/or combinations thereof. A particularly preferred selective AT1 receptor antagonist is olmesartan.

FIGURES

FIG. 1: Kaplan Meier survival curves. Low dose Compound-21 significantly reduced mortality compared to placebo.

Figure 2:
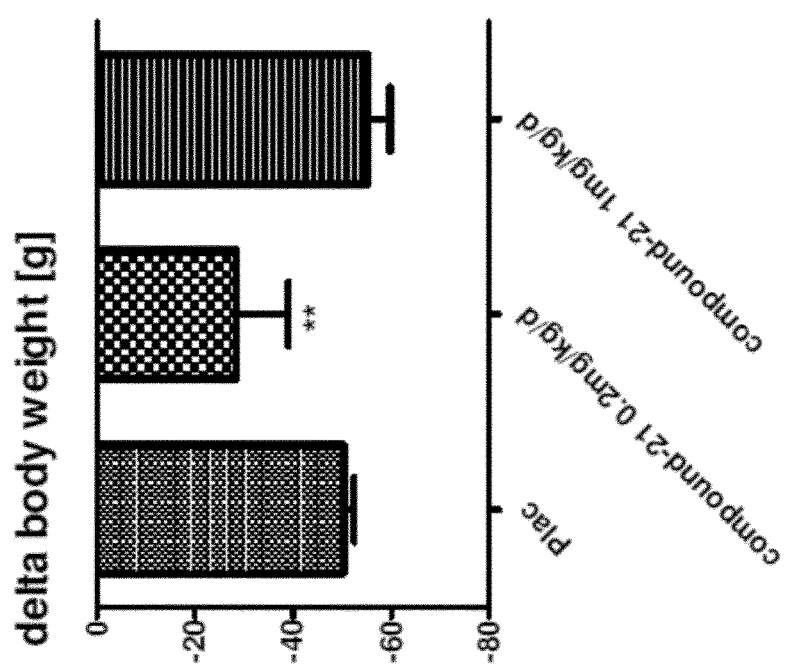

FIG. 2: change in body weight during the experiment. Compound-21 at 0.2 mg/kg/d significantly reduced loss of body weight. **: $p<0.01$ vs placebo.

Figure 3:
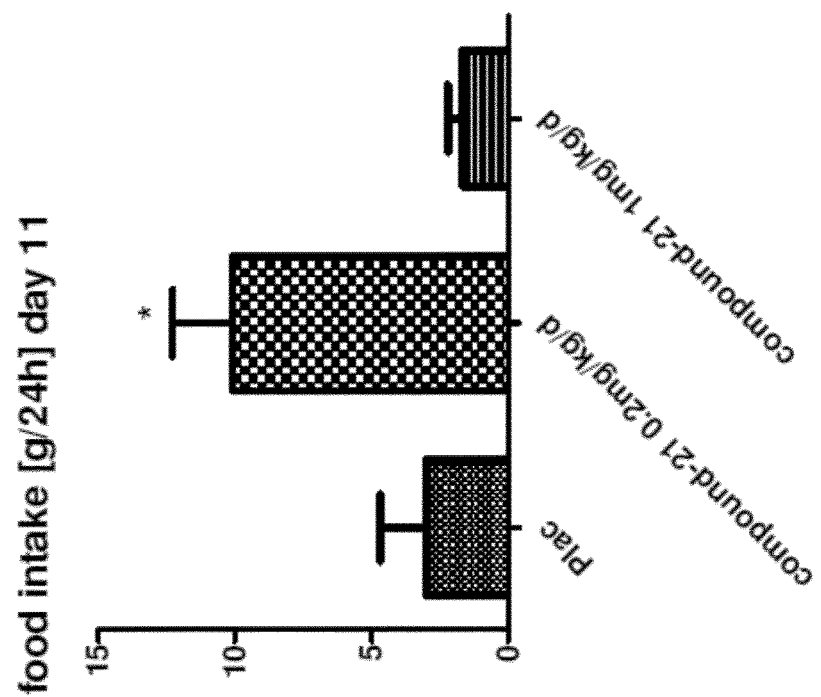

FIG. 3: food intake on day 11 after tumor inoculation. Compound-21 at 0.2 mg/kg/d significantly increased food intake. *: $p<0.05$ vs placebo. A higher food intake can be seen as a marker for improved quality of life FIG. 4: spontaneous locomotor activity on day 11 after tumor inoculation. Compound-21 at 0.2 mg/kg/d significantly increased activity. *: $p<0.05$ vs placebo. Increased activity can be seen as a marker for improved quality of life FIG. 5: heart weight at the end of the study. Compound-21 at 0.2 mg/kg/d significantly increased heart weight. *: $p<0.05$ vs placebo. Protection of cardiac weight indicates improved cardiac function compared to placebo FIG. 6: weight of the mixed fiber type gastrocnemius at the end of the study. Compound-21 at 0.2 mg/kg/d significantly increased gastrocnemius weight. **: $p<0.01$ vs placebo.

Figure 7:
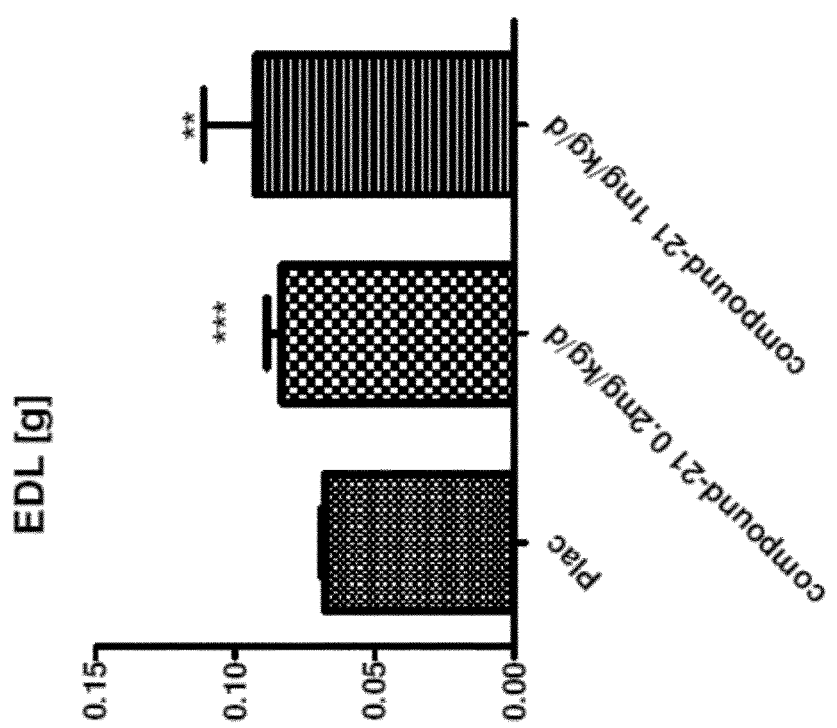

FIG. 7: weight of the fast fiber type EDL at the end of the study. Compound-21 at 0.2 mg/kg/d significantly increased EDL weight. Interestingly, high dose also improved EDL weight. : $p<0.01$, *: $p<0.001$ vs placebo.

Figure 8:
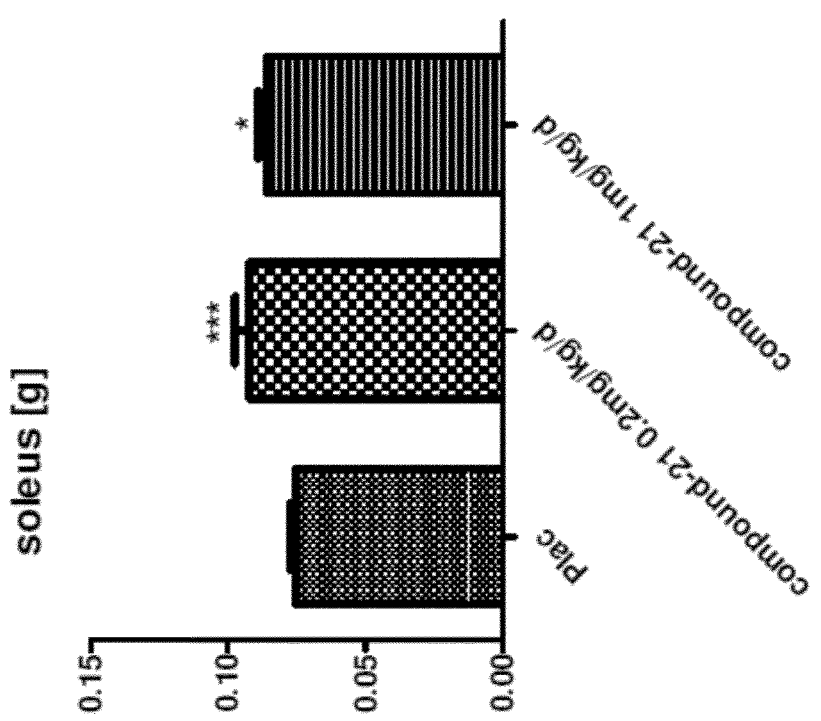

FIG. 8: weight of the slow fiber type soleus at the end of the study. Compound-21 at 0.2 mg/kg/d significantly increased soleus weight. Interestingly, high dose also improved soleus weight. *: $p<0.05$, ***: $p<0.01$ vs placebo.

Figure 9:
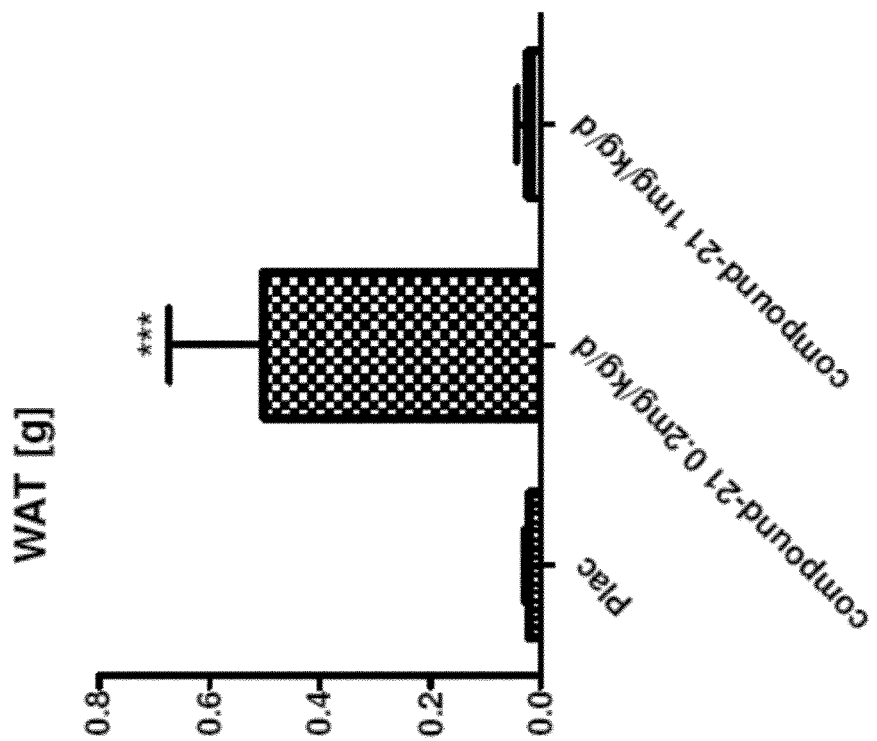

FIG. 9: weight of white adipose tissue (WAT) epididymal fat at the end of the study. Compound-21 at 0.2 mg/kg/d significantly increased WAT weight. ***: $p<0.001$ vs placebo.

Figure 10:
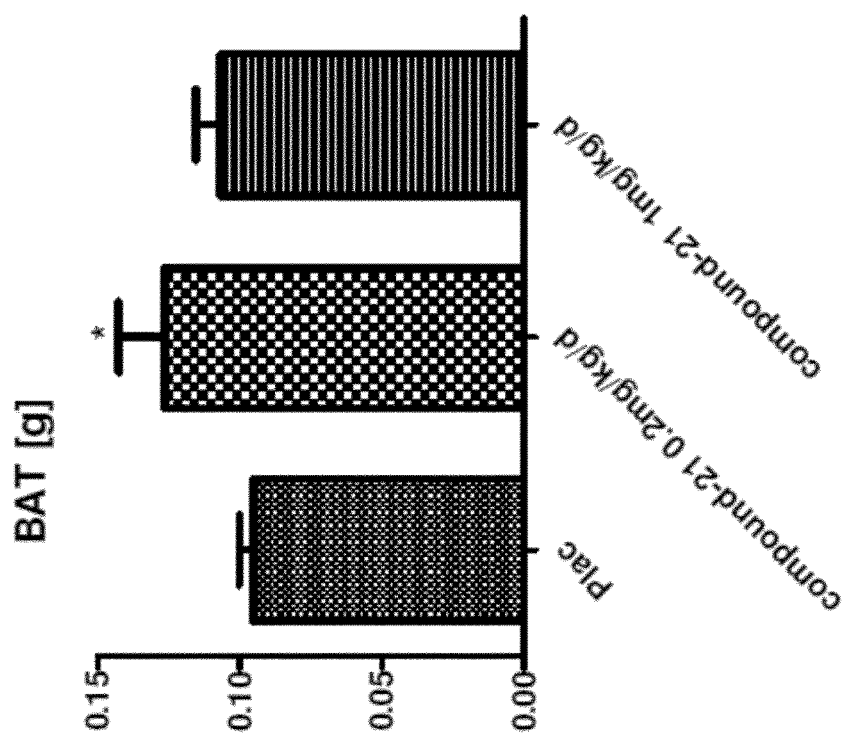

FIG. 10: weight of brown adipose tissue (BAT) at the end of the study. Compound-21 at 0.2 mg/kg/d significantly increased BAT weight. *: $p<0.05$ vs placebo.

Figure 11:
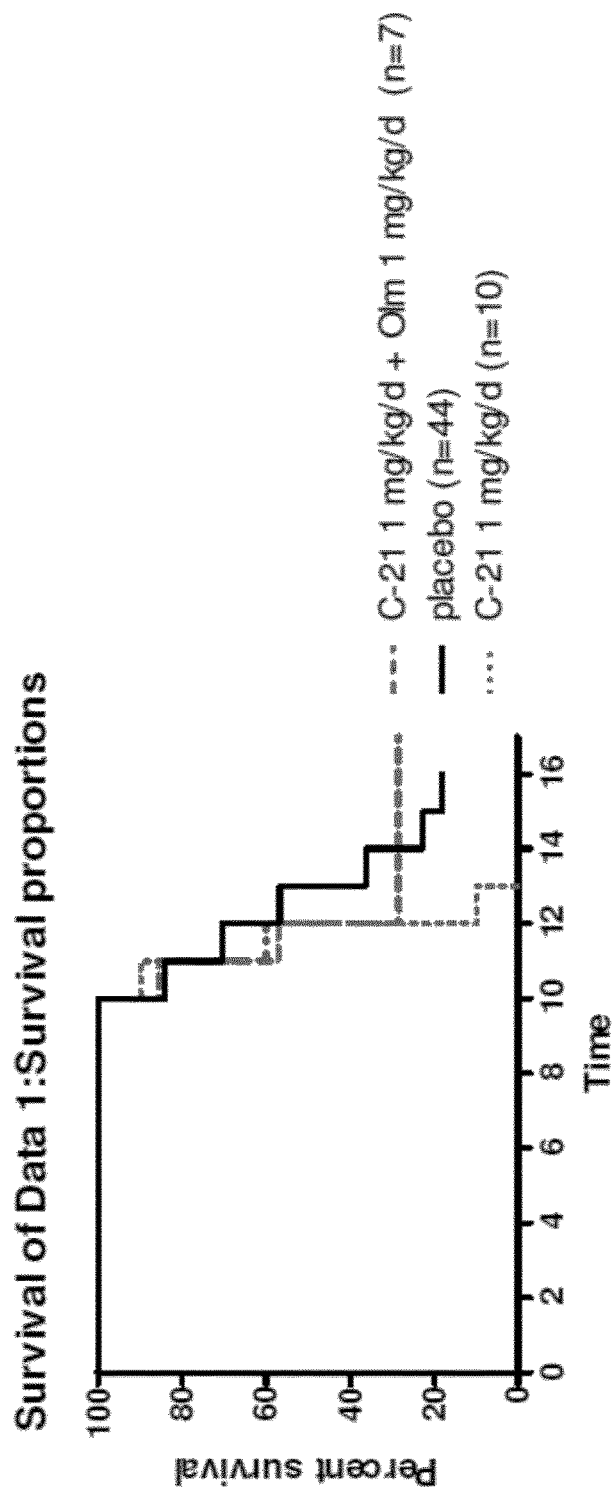

FIG. 11: Kaplan Meier survival curves. High dose Compound-21 can be combined with an AT1-Blocker to improve survival FIG. 12: The combination treatment reduced loss of body weight. **: $p<0.01$.

Figure 13:
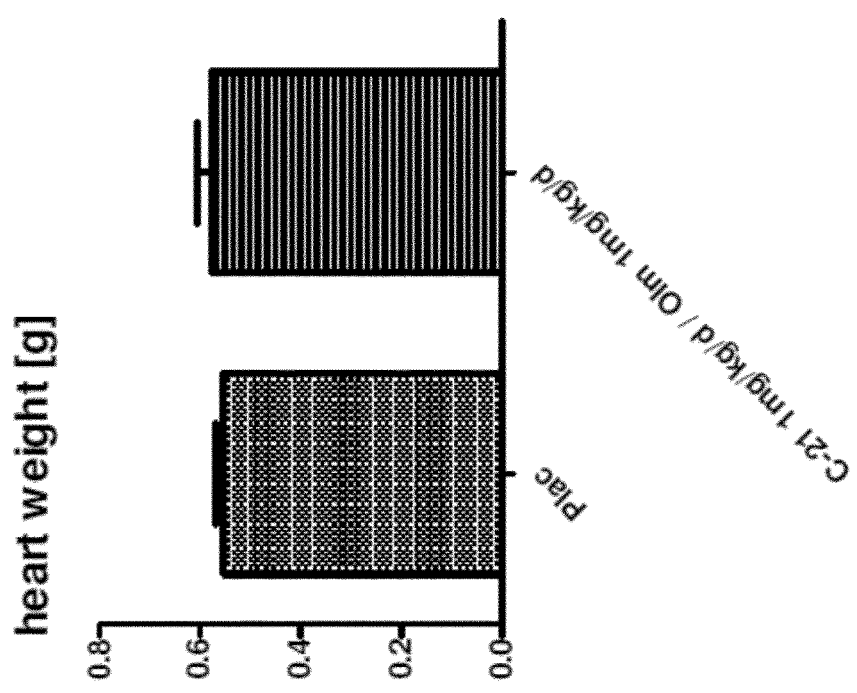

FIG. 13: heart weight was similar in both groups.

Figure 14:
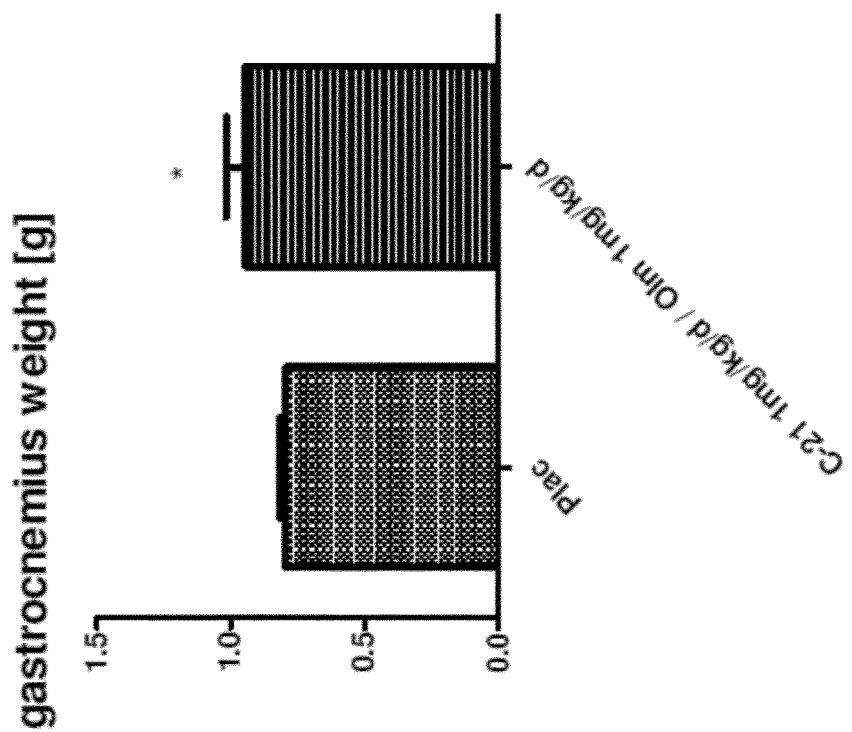
Figure 15:
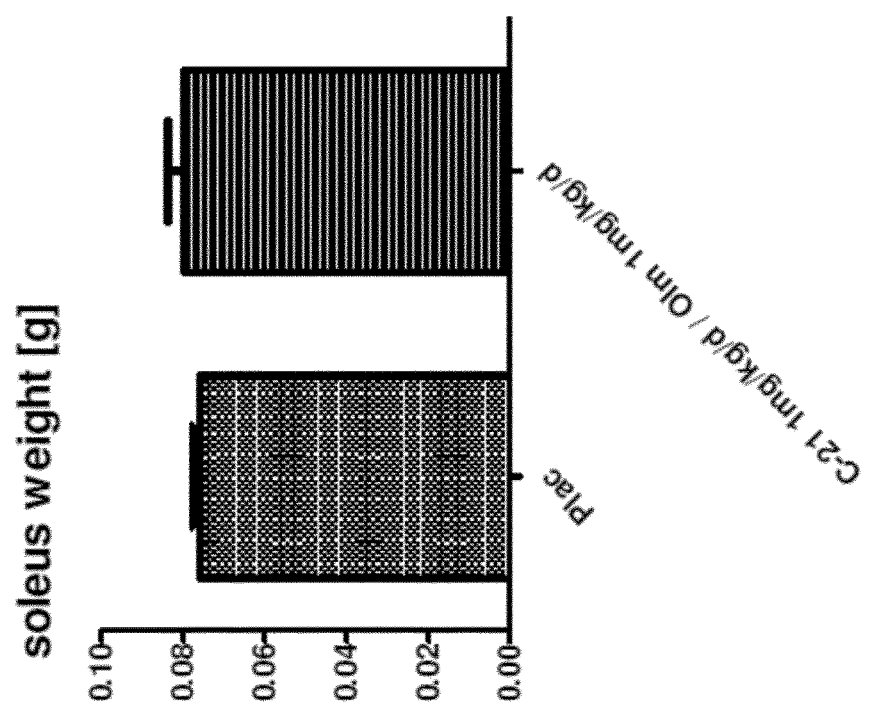

FIG. 14: Weight of the mixed fiber type muscle gastrocnemius was higher in the treated group. *: $p<0.05$ FIG. 15: Weight of the slow fiber type muscle soleus was unchanged between groups.

Figure 16:
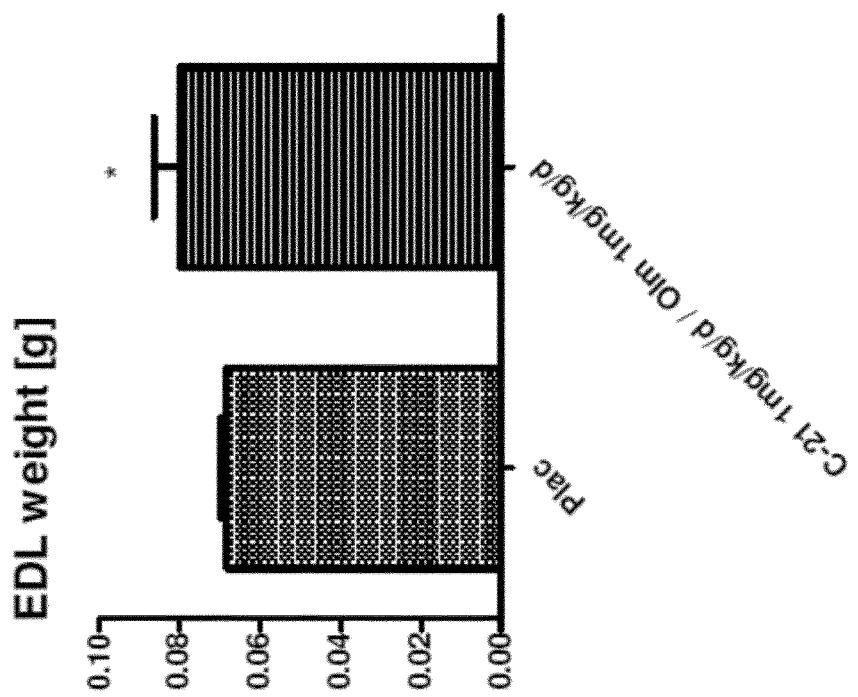

FIG. 16: Weight of the mixed fiber type muscle gastrocnemius was higher in the treated group. *: $p<0.05$ FIG. 17: Weight of white adipose tissue was higher (here epididymal fat) in the treated group. *: $p<0.05$ FIG. 18: Treatment had no effect on the weight of brown adipose tissue (BAT).

EXAMPLES

Example 1

A person skilled in the art would expect overall beneficial effects from ACE inhibition in the context of cachexia therapy, based on the results in chronic heart failure and the human imidapril data.

In our lab, using the AH-130 Yoshida hepatoma cancer cachexia rat model, we also observed a dose-dependent reduction of body weight loss by imidapril. However, the animals surprisingly showed a worse hazard ratio and survival compared to untreated tumor-bearing animals. Also, imidapril did not improve quality of life (activity and food intake). This indicates that angiotensin II may indeed be of importance to wasting process, as seen in direct stimulation of myotubes. Use of an ACE inhibitor blocks all activation of both the AT1 and AT2 receptors, therefore inhibiting the beneficial effects of angiotensin II mediated activation of the AT2 receptor.

It would be preferable to use an agonist of the AT2 receptor, which may mediate cell survival and has anti-inflammatory properties. An important feature of cachexia is a chronic inflammatory state, in which cytokines like IL-1, IL-6, TNF-alpha and interferon-gamma contribute to an induction of catabolism and apoptosis in skeletal muscle. This induction of cytokines is regulated by NFkB signaling that is inhibited by activation of downstream pathways of the AT2 receptor.

Hence, this invention related to the use of AT2 agonists to prevent and/or treat cachexia (with the exception of inflammatory bowel syndrome) and more specifically cancer cachexia. This compound could be any one of the compounds mentioned in patent US 2009/0326026 owned by Vicore Pharma AB. The preferred substance being Compound 21, depicted below:

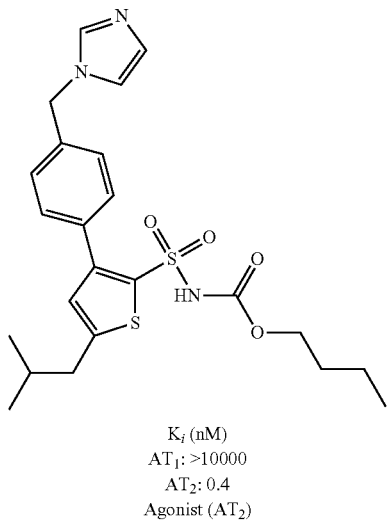 [SMILES: CCCCOC(=O)NS(=O)(=O)c1sc(CC(C)C)cc1-c1ccc(Cn2ccnc2)cc1]

$K_i$ (nM)
$AT_1$: >10000
$AT_2$: 0.4
Agonist ($AT_2$)

Any selective AT2 agonist, the preferred substance being Compound 21, will improve cachexia symptoms by reducing muscle wasting, preserving fat mass and improving quality of life. These beneficial effects will ultimately lead to a better outcome in cachexia.

Example 2

Study Plan:

The ascites hepatoma Yoshida AH-130 cells ($10^8$) were inoculated into approx. 200 g male Wistar rats. Alternatively animals received saline injection only (sham). The animals were housed in groups of three. The day after inoculation animals were randomized into various groups as described in the methods. The rats then received treatment with either placebo (n=44) or compound-21 (0.2 or 1.0 mg/kg/d n=15 or 10, respectively) over a period maximal 16 days. The primary endpoints of the study included survival and quality of life. Secondary endpoints included body weight and body composition as well as organ weight, which were assessed at the end of the study (or after death).

Figure 4:
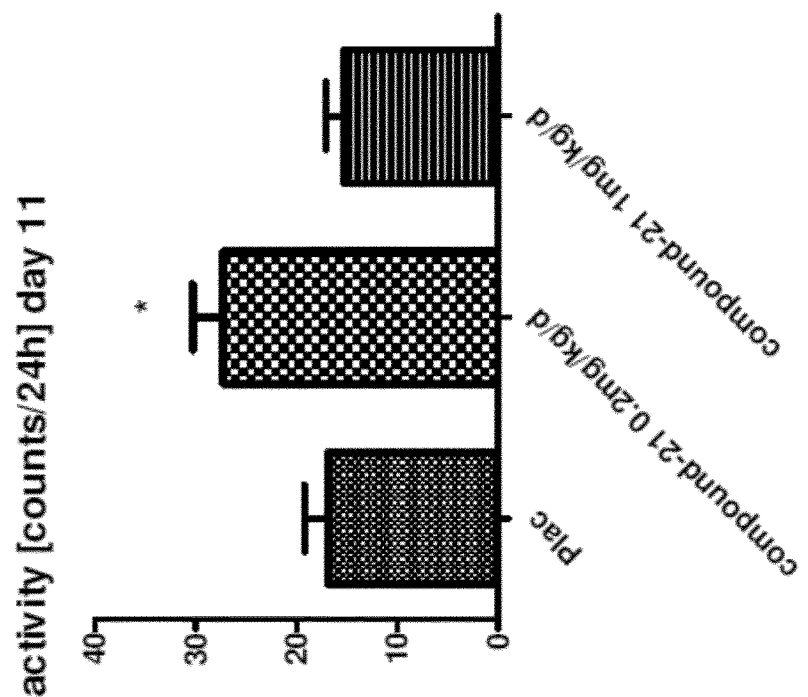
Figure 5:
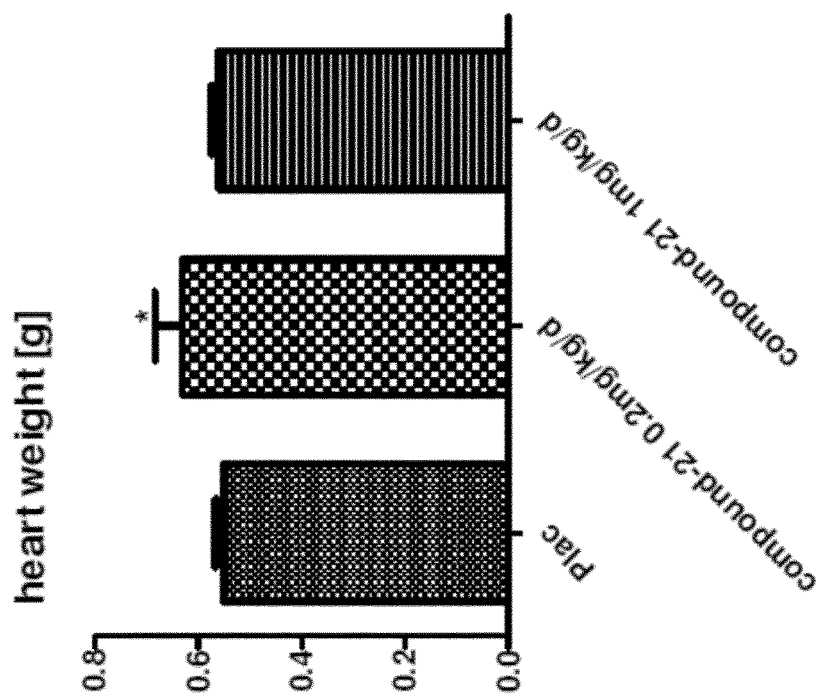
Figure 6:
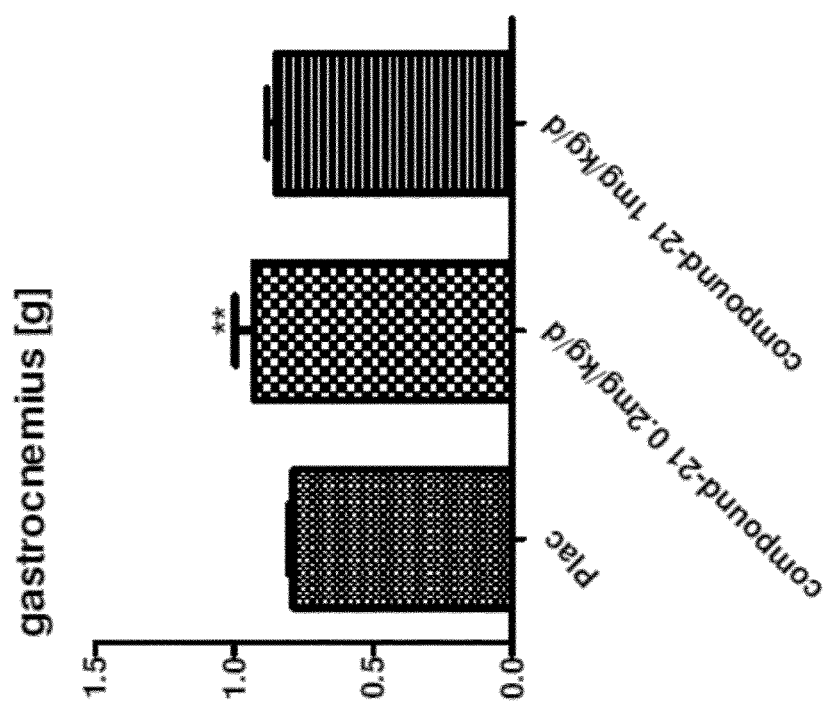

Results 0.2 mg/kg/day compound-21 significantly improved survival in the Yoshida hepatoma cancer cachexia model (0.2 mg compound-21 vs placebo: HR: 0.45 95% Cl: 0.22-0.92, p=0.0275), whilst a higher dose compound-21 was not effective (FIG. 1). This is clearly due to overdosing the compound leading to toxic effects. Rats showed no difference in baseline body weight. Loss of body weight was attenuated by 0.2 mg/kg/d compound-21 compared to untreated tumor-bearing animals (FIG. 2). Food intake and spontaneous activity were significantly improved compared to placebo (FIGS. 3, 4). This indicates an improved quality of life. Heart weight was improved by compound-21 (FIG. 5) The weights of the mixed fiber type muscle gastrocnemius, the fast fiber type EDL and the slow fiber type soleus were all higher compared to placebo (FIG. 6-8). Interestingly, high dose also improved EDL and soleus weight (FIGS. 7,8). Both white and brown fat were improved by 0.2 mg/kg/d compound-21 (FIGS. 9,10). The preservation of both muscle and fat mass as well as the improved quality of life and survival makes compound-21 an ideal drug for cancer cachexia.

Example 3

Study Plan:

The ascites hepatoma Yoshida AH-130 cells ($10^8$) were inoculated into approx. 200 g male Wistar rats. Alternatively animals received saline injection only (sham). The animals were housed in groups of three. The day after inoculation animals were randomized. The rats then received treatment with either placebo (n=44) or 1 mg/kg/d compound-21 in combination with 1 mg/kg/d olmesartan over a period maximal 16 days. The primary endpoints of the study included survival and quality of life. Secondary endpoints included body weight and body composition as well as organ weight, which were assessed at the end of the study (or after death).

Results

Figure 12:
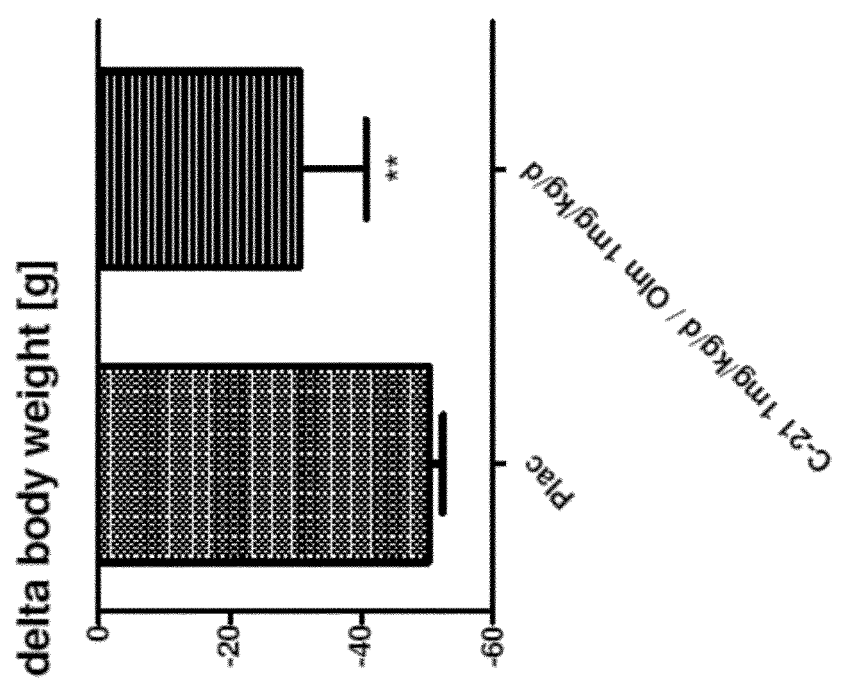
Figure 17:
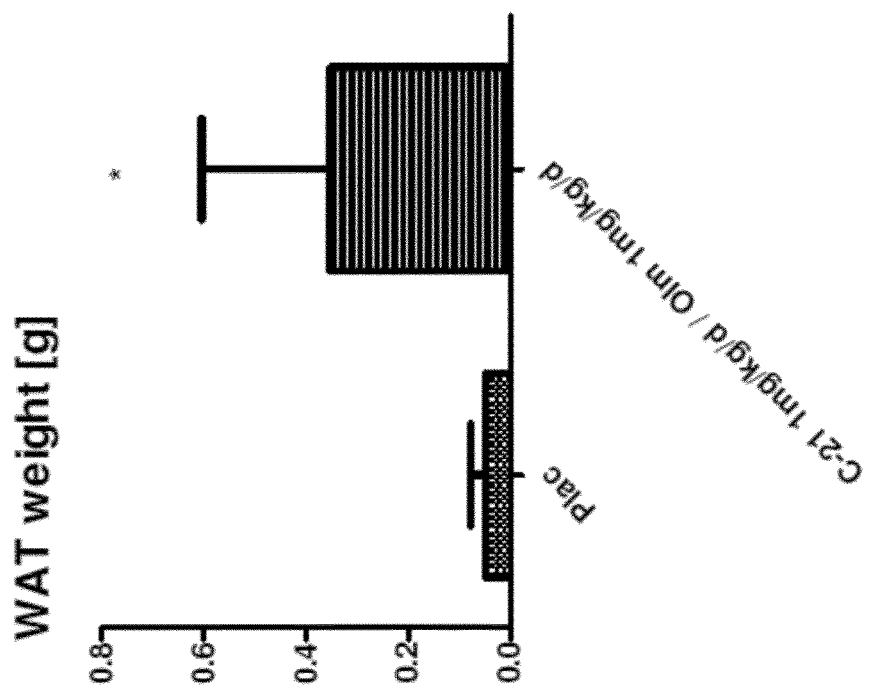
Figure 18:
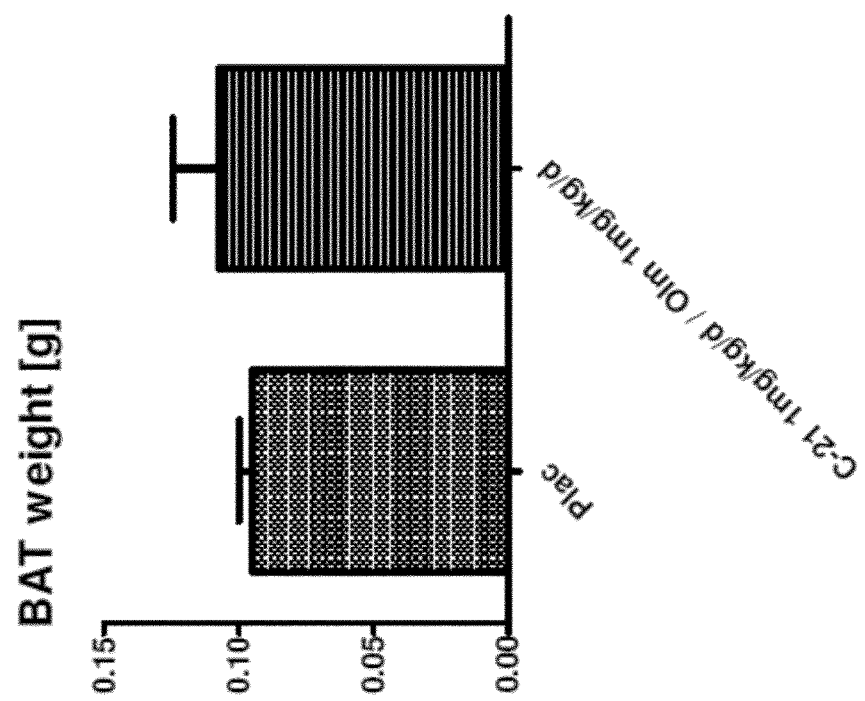

The results of a combined treatment with 1 mg/kg/d compound-21 (C-21) and 1 mg/kg/d olmesartan show an improved survival compared to 1 mg/kg/d C-21 alone (HR 0.53, 95% Cl: 0.14-2.09; FIG. 11). The loss of body weight was reduced compared to untreated tumour-bearing rats (FIG. 12). Heart weight was similar in both groups (FIG. 13). Weight of the mixed fiber type muscle gastrocnemius was increased in the treated group (FIG. 14), the slow fiber type soleus showed nor differences (FIG. 15) and the fast fiber type EDL had an increased mass in the treated group (FIG. 16). White, but not brown, adipose tissue was preserved in treated rats (FIGS. 17, 18).

In a More Preferred Embodiment the AT2 Receptor Agonist is Combined with a an ACE Inhibitor or Even More Preferred a Highly Selective AT1 Receptor Antagonist In cachexia of various underlying diseases, including cancer, elevated angiotensin II levels have been described patent WO 00/21509. Elevated angiotensin II levels would result in an activation of AT1 and AT2 receptors. Since the AT1 receptor is more abundantly expressed in all tissues, the detrimental AT1 effects may prevail over the beneficial AT2 effect, even if the patients is treated with a highly selective AT2 agonist, such as Compound 21. Therefore a combination therapy may be more beneficial and may therefore more preferred. This drug combination consists of:

1) A combination of any ACE inhibitor and a selective AT2 agonist, the preferred being Compound 21.
2) A combination of any highly selective AT1 antagonist and a selective AT2 agonist, the preferred being Compound 21.

The invention claimed is:

1. A method of treatment of cachexia, wherein a patient in need of such therapy is administered an effective dose of a selective AT2 receptor agonist or a pharmaceutically acceptable salt thereof, wherein the selective AT2 receptor agonist is a compound of formula I:

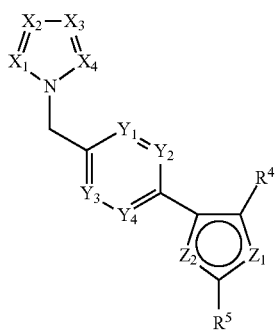

wherein
one of $X_1$ and $X_2$ represents —N— and the other represents —C($R^1$)—;
$X_3$ represents —N— or —C($R^2$)—;
$X_4$ represents —N— or —C($R^3$)—;
$R^1$, $R^2$ and $R^3$ independently represent H, $C_{1-6}$ alkyl, $C_{1-6}$ alkoxy, $C_{1-6}$ alkoxy-$C_{1-6}$-alkyl or halo;
provided that, when $X_1$ represents —C($R^1$)—, $X_3$ represents —C($R^2$)— and $X_4$ represents —C($R^3$)—, then $R^1$ represents H;
$Y_1$, $Y_2$, $Y_3$ and $Y_4$ independently represent CH— or —CF;
$Z_1$ represents —CH—, —O—, —S—, —N— or —CH=CH—;
$Z_2$ represents —CH—, —O—, —S— or —N—;
provided that:
(a) $Z_1$ and $Z_2$ are not the same;
(b) when $Z_1$ represents —CH=CH—, then $Z_2$ may only represent —CH— or N—; and
(c) other than in the specific case in which $Z_1$ represents —CH=CH—, and $Z_2$ represents —CH—, when one $Z_1$ and $Z_2$ represents —CH—, then the other represents —O— or —S—;
$R^4$ represents —S(O)$_2$N(H)C(O)$R^6$, —S(O)$_2$N(H)S(O)$_2$ $R^6$, —C(O)N(H)S(O)$_2R^6$, or, when $Z_1$ represents —CH=CH—, $R^4$ may represent —(H)S(O)$_2$N(H)C(O)$R^7$ or —N(H)C(O)N(H)S(O)$_2R^7$;
$R^5$ represents $C_{1-6}$ alkyl, $C_{1-6}$ alkoxy, $C_{1-6}$ alkoxy-$C_{1-6}$-alkyl or di-$C_{1-3}$alkylamino-$C_{1-4}$-alkyl;
$R^6$ represents $C_{1-6}$ alkyl, $C_{1-6}$ alkoxy, $C_{1-6}$ alkoxy-$C_{1-6}$-alkyl, $C_{1-3}$ alkoxy-$C_{1-6}$-alkoxy, $C_{1-6}$ alkylamino or di-$C_{1-6}$ alkylamino; and
$R^7$ represents $C_{1-6}$ alkyl,
wherein
alkyl groups, and the alkyl parts of alkoxy, alkoxyalkyl, alkoxyalkoxy, alkylamino and alkylaminoalkyl groups, as defined herein may be straight-chain or, when there is a minimum of three carbon atoms, be branched-chain, and/or cyclic; or when there is a minimum of four carbon atoms, such groups may also be part cyclic/acyclic; or alkyl groups, and alkyl parts of alkoxy, alkoxyalkyl, alkoxyalkoxy, alkylamino and alkylaminoalkyl groups, may also be saturated or, when there is a minimum of two carbon atoms, be unsaturated; or such groups may also be substituted by one or more halo, and especially fluoro, atoms.

2. The method of claim 1, wherein X1 represents —C(R1)-, X2 represents N, X3 represents —C(R2)-, and X4 represents —C(R3)-.

3. The method of claim 1, wherein $R^1$, $R^2$ and $R^3$ are all H.

4. The method of claim 1, wherein $Y_1$, $Y_2$, $Y_3$ and $Y_4$ all represent —CH—.

5. The method of claim 1, wherein $Z_1$ represents —S— and $Z_2$ represents —CH—.

6. The method of claim 1, wherein $R^4$ represents —S(O)$_2$N(H)C(O)$R^6$, $R^5$ represents iso-butyl, and $R^6$ represents n-butoxy.

7. The method of claim 1, wherein $X_2$ represents N, $X_1$, $X_3$ and $X_4$ all represent —CH—; $Y_1$, $Y_2$, $Y_3$ and $Y_4$ all represent —CH—; $Z_1$ represents —S—; $Z_2$ represents —CH—; $R^4$ represents —S(O)$_2$N(H)C(O)$R^6$; $R^5$ represents iso-butyl; and $R^6$ represents n-butoxy.

8. A method of treatment of cachexia, wherein a patient in need of such therapy is administered an effective dose of a selective AT2 receptor agonist or a pharmaceutically acceptable salt thereof in combination with at least one further active pharmaceutical agent, wherein the selective AT2 receptor agonist is a compound of formula I:

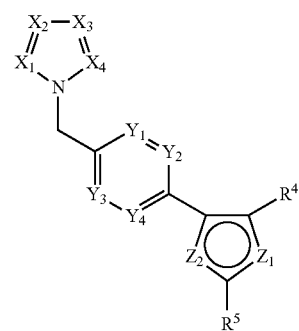

wherein
one of $X_1$ and $X_2$ represents —N— and the other represents —C($R^1$)—;
$X_3$ represents —N— or —C($R^2$)—;
$X_4$ represents —N— or —C($R^3$)—;
$R^1$, $R^2$ and $R^3$ independently represent H, $C_{1-6}$ alkyl, $C_{1-6}$ alkoxy, $C_{1-6}$ alkoxy-$C_{1-6}$-alkyl or halo;
provided that, when $X_1$ represents —C($R^1$)—, $X_3$ represents —C($R^2$)— and $X_4$ represents —C($R^3$)—, then $R^1$ represents H;
$Y_1$, $Y_2$, $Y_3$ and $Y_4$ independently represent —CH— or —CF;
$Z_1$ represents —CH—, —O—, —S—, —N— or —CH=CH—;
$Z_2$ represents —CH—, —O—, —S— or —N—;
provided that:
(a) $Z_1$ and $Z_2$ are not the same;
(b) when $Z_1$ represents —CH=CH—, then $Z_2$ may only represent —CH— or N—; and
(c) other than in the specific case in which $Z_1$ represents —CH=CH—, and $Z_2$ represents —CH—, when one $Z_1$ and $Z_2$ represents —CH—, then the other represents —O— or —S—;
$R^4$ represents —S(O)$_2$N(H)C(O)$R^6$, —S(O)$_2$N(H)S(O)$_2$ $R^6$, —C(O)N(H)S(O)$_2R^6$, or, when $Z_1$ represents —CH=CH—, $R^4$ may represent —(H)S(O)$_2$N(H)C(O)$R^7$ or —N(H)C(O)N(H)S(O)$_2R^7$;
$R^5$ represents $C_{1-6}$ alkyl, $C_{1-6}$ alkoxy, $C_{1-6}$ alkoxy-$C_{1-6}$-alkyl or di-$C_{1-3}$alkylamino-$C_{1-4}$-alkyl;

$R^6$ represents $C_{1-6}$ alkyl, $C_{1-6}$ alkoxy, $C_{1-6}$ alkoxy-$C_{1-6}$-alkyl, $C_{1-3}$ alkoxy-$C_{1-6}$-alkoxy, $C_{1-6}$ alkylamino or di-$C_{1-6}$ alkylamino; and $R^7$ represents $C_{1-6}$ alkyl, wherein alkyl groups, and the alkyl parts of alkoxy, alkoxyalkyl, alkoxyalkoxy, alkylamino and alkylaminoalkyl groups, as defined herein may be straight-chain or, when there is a minimum of three carbon atoms, be branched-chain, and/or cyclic; or when there is a minimum of four carbon atoms, such groups may also be part cyclic/acyclic; or alkyl groups, and alkyl parts of alkoxy, alkoxyalkyl, alkoxyalkoxy, alkylamino and alkylaminoalkyl groups, may also be saturated or, when there is a minimum of two carbon atoms, be unsaturated; or such groups may also be substituted by one or more halo, and especially fluoro, atoms.

9. The method of claim 8, wherein said at least one further active pharmaceutical agent is an angiotensin converting enzyme (ACE) inhibitor.

10. The method of claim 8, wherein the ACE inhibitor is one of captopril, zofenopril, enalapril, ramipril, quinapril, perindopril, lisinopril, benazepril, imidapril, trandolapril, fosinopril, moexipril, cilazapril, spirapril, temocapril, alacepril, ceronapril, delepril, moveltipril, and/or combinations thereof.

11. The method of claim 8, wherein said at least one further active pharmaceutical agent is a selective AT1 receptor antagonist.

12. The method of claim 8, wherein said at least one further active pharmaceutical agent is one of azilsartan, candesartan, eprosartan, fimasartan, irbesartan, losartan, milfasartan, olmesartan, pomisartan, pratosartan, ripiasartan, saprisartan, tasosartan, telmisartan, valsartan and/or combinations thereof.

13. The method of claim 1, wherein cachexia is cachexia associated with cancer, AIDS, liver cirrhosis, liver failure, chronic renal failure, chronic infection, diabetes, heart disease, chronic obstructive lung disease, multiple sclerosis, tuberculosis, familial amyloid polyneuropathy, heavy metal poisoning, arthritis, motor neuron diseases, burns and hormonal deficiency syndromes.

14. The method of claim 1, wherein cachexia is cancer cachexia.

15. The method of claim 8, wherein X1 represents —C(R1)-, X2 represents N, X3 represents —C(R2)-, and X4 represents —C(R3)-.

16. The method of claim 8, wherein $R^1$, $R^2$ and $R^3$ are all H.

17. The method of claim 8, wherein $Y_1$, $Y_2$, $Y_3$ and $Y_4$ all represent —CH—.

18. The method of claim 8, wherein $Z_1$ represents —S— and $Z_2$ represents —CH—.

19. The method of claim 8, wherein $R^4$ represents —S(O)$_2$N(H)C(O)R$^6$, $R^5$ represents iso-butyl, and $R^6$ represents n-butoxy.

20. The method of claim 8, wherein $X_2$ represents N, $X_1$, $X_3$ and $X_4$ all represent —CH—; $Y_1$, $Y_2$, $Y_3$ and $Y_4$ all represent —CH—; $Z_1$ represents —S—; $Z_2$ represents —CH—; $R^4$ represents —S(O)$_2$N(H)C(O)R$^6$; $R^5$ represents iso-butyl; and $R^6$ represents n-butoxy.

* * * * *